United States Patent [19]

Masuda

[11] Patent Number: 5,781,657
[45] Date of Patent: Jul. 14, 1998

[54] APPARATUS FOR INSPECTING PATTERN OF PHOTOMASK AND METHOD THEREFOR

[75] Inventor: Satoshi Masuda, Tokyo, Japan

[73] Assignee: Kabushiki Kaisha Toshiba, Kawasaki, Japan

[21] Appl. No.: 956,492

[22] Filed: Oct. 22, 1997

Related U.S. Application Data

[63] Continuation of Ser. No. 494,590, Jun. 23, 1995, abandoned, which is a continuation of Ser. No. 160,728, Dec. 2, 1993, abandoned.

[30] Foreign Application Priority Data

Dec. 4, 1992 [JP] Japan .................... 4-324548

[51] Int. Cl.$^6$ .............. G06K 9/00; H04N 7/18; G01B 11/00
[52] U.S. Cl. .......... 382/147; 348/126; 348/130; 382/145; 382/149; 356/389
[58] Field of Search .................. 382/141, 144, 382/145, 147, 149; 348/86, 87, 126, 130; 356/389; 364/550, 559, 571.04, 491; 29/833; 438/16

[56] References Cited

U.S. PATENT DOCUMENTS

| | | | |
|---|---|---|---|
| 3,997,912 | 12/1976 | Zsagar | 358/78 |
| 4,479,145 | 10/1984 | Azuma et al. | 358/106 |
| 4,718,767 | 1/1988 | Hazama | 356/381 |
| 4,805,123 | 2/1989 | Specht et al. | 364/559 |
| 4,962,541 | 10/1990 | Doi et al. | 382/30 |
| 5,119,434 | 6/1992 | Bishop et al. | 382/8 |
| 5,163,102 | 11/1992 | Yamazaki et al. | 382/8 |
| 5,253,306 | 10/1993 | Nishio | 348/129 |
| 5,286,581 | 2/1994 | Lee | 430/5 |
| 5,321,767 | 6/1994 | Murase | 382/8 |
| 5,379,348 | 1/1995 | Watanabe et al. | 382/144 |
| 5,442,714 | 8/1995 | Iguchi | 382/144 |
| 5,481,624 | 1/1996 | Kamon | 382/144 |

*Primary Examiner*—Bipin Shalwala
*Attorney, Agent, or Firm*—Finnegan, Henderson, Farabow, Garrett & Dunner, L.L.P.

[57] ABSTRACT

Graphic data for forming a light-shielding pattern and graphic data for forming a semitransparent pattern are stored in first and second memories, respectively. A synthesis circuit converts the graphic data stored in the first and second memories into bit patterns and writes them in a third memory. A line width determination circuit determines, as a halftone region, a region having the number of continuous bits at the same level, which number is a predetermined number or less, in the bit patterns stored in the third memory. A pattern data generation circuit generates pattern data constituted by the signal levels of a light-transmitting region and a light-shielding region on the basis of an output signal from the synthesis circuit. A pattern data correction circuit corrects the signal level of the pattern data corresponding to the halftone region designated by the line width determination circuit to a signal level corresponding to a semitransparent film in accordance with the transmittance of the semitransparent film. A comparator compares the corrected pattern data output from the pattern data correction circuit with a signal output from a line sensor and corresponding to a halftone type phase shift mask to be inspected, thereby inspecting the patterns.

18 Claims, 3 Drawing Sheets

APPARATUS FOR INSPECTING PATTERN OF PHOTOMASK AND METHOD THEREFOR

This application is a continuation of application Ser. No. 08/494,590, filed Jun. 23, 1995, now abandoned, which is a continuation of Ser. No. 08/160,728, filed Dec. 2, 1993, now abandoned.

BACKGROUND OF THE INVENTION

1. Field of the Invention

The present invention relates to an apparatus for inspecting a photomask, in particular, a halftone type phase shift mask, used in an exposing process for a wafer, and a method therefor.

2. Description of the Related Art

A photomask is manufactured using an electron beam drawing apparatus (to be referred to as an EB drawing apparatus hereinafter) in the following manner. That is, a blank in which a light-shielding film constituted by a multilayered thin film consisting of chromium oxide and chromium films is formed on a glass substrate. An EB resist is coated on the blank, and a pattern is drawn on the blank by the EB drawing apparatus. Thereafter, the resist is developed to form a resist pattern, and the light-shielding film is etched using the resist pattern as a mask. After the resist pattern is removed, the resultant structure is subjected to a cleaning process so as to be sent to a pattern inspection process. In this pattern inspection process, patterns are inspected for any defects and shape errors, the dimensional ratios of the patterns are measured, and appearance inspection is performed. As a result, photomasks satisfying given standards are shipped, and they are used in an exposing process for wafers.

The types of inspection for the defects and shapes of the patterns are roughly classified into chip comparison inspection, mask comparison inspection, and data comparison inspection. In the chip comparison inspection, when the same patterns are repetitively arranged within the surface of a photomask, the patterns are inspected by comparing them with each other. In the mask comparison inspection, the two same masks are set next to each other and inspected by comparing them with each other. In the data comparison inspection, the light intensity of graphic data used in EB drawing is compared with that of light on an exposed surface.

Since the present invention relates to the data comparison inspection, the data comparison inspection will be described below in detail.

FIGS. 3A to 3D are views for explaining a method of performing data comparison inspection of the pattern of a conventional photomask. FIG. 3A is a sectional view of the photomask. A pattern 31 is formed on a glass substrate 30 by a metallic light-shielding film.

FIG. 3B shows graphic data for etching the light-shielding film of a blank to form the pattern 31 shown in FIG. 3A. An EB resist (not shown) coated on the light-shielding film is exposed by an electron beam in a region corresponding to level "1" of the graphic data, and the light-shielding film is not exposed by the electron beam in a region corresponding to level "0". When the EB resist is developed, the resist at a portion exposed by the electron beam is removed. The non-exposed portion is left on the light-shielding film to form a resist pattern. When the metallic light-shielding film is etched using the resist pattern, as shown in FIG. 3A, the pattern 31 consisting of the light-shielding film is formed at the portion corresponding to level "0" of the graphic data, thereby completing a photomask.

FIG. 3C is a graph of an output from a line sensor which is obtained when an inspection beam is radiated on the photomask, and the beam passing through the photomask is received by a line sensor. The line sensor is constituted by a plurality of photoelectric conversion cells arranged in a line. As shown in FIG. 3C, the distribution characteristics of a light intensity obtained by the output from the line sensor cannot be expressed in the binary system unlike graphic data. This is because the beam is diffracted at the boundary of the light-shielding film when the inspection beam is radiated on the photomask, and a region where brightness changes from a dark portion to a bright portion is formed by the diffraction of the transmitted light near the boundary between a dark portion formed on a cell at a position corresponding to level "0" of the graphic data and a bright portion formed on a cell at a position corresponding to level "1" of the graphic data.

Therefore, the pattern data of the transmitted beam formed on the line sensor when the inspection beam is actually radiated on the photomask are formed in units of cells on the basis of the graphic data. To obtain the pattern data, the intensity of an output signal corresponding to the dark portion formed on the line sensor by the light-shielding film and the intensity of an output signal corresponding to the bright portion formed on the line sensor by a light-transmitting region having no light-shielding film are measured, and they are used as the pattern data of the bright and dark portions. Pattern data for a cell of the line sensor corresponding to a region where brightness changes and in which data having levels "0" and "1" are adjacent to each other is determined by calculation using the signal intensities of the bright and dark portions.

FIG. 3D shows pattern data corresponding to FIG. 3C. In pattern inspection for a photomask, the pattern data is compared with a signal output from the line sensor when an inspection beam is radiated on the photomask. In this inspection, when the difference between the pattern data and the output signal from the line sensor is calculated, if the absolute value of this difference exceeds a predetermined threshold value, that portion of the photomask, which relates to this absolute value exceeding the predetermined threshold value, is determined as a defective. Therefore, as the threshold value is smaller, the defect detection sensitivity is higher.

According to the above inspection method, a photomask constituted by only a light-shielding region having a light-shielding film and a light-transmitting region having no light-insulating film can be inspected. However, some phase shift masks which can be subjected to exposure for micropatterns, and which have been used in recent years, cannot be inspected by the above inspection method unless the defect detection sensitivity is lowered.

That is, a halftone type phase shift mask is known as one of various types of phase shift masks. When this halftone type shift mask is used, a steep light intensity distribution is formed by making a light-shielding portion have a certain transmittance, thereby forming a sharp pattern. The effect of forming a sharp pattern depends on the line width of the pattern, and the maximum line width is about 0.4 to 0.5 μm. When the line width is larger than the maximum line width, the effect is reduced.

For this reason, in the halftone type phase shift mask, a pattern region whose line width is larger than 0.5 μm is formed by a light-shielding film such as a chromium film which completely shields light, and a pattern region whose line width is 0.5 μm or less is formed a semitransparent film consisting of a semitransparent material having a certain transmittance. As a result, patterns having different transmittances are present in the surface of the normal halftone type phase mask.

FIG. 4A is a sectional view showing a halftone type phase shift mask, and FIG. 4B is a graph showing a light intensity distribution obtained when an inspection beam is radiated on this halftone type phase shift mask. Referring to FIG. 4A, a light-shielding film 41 and a semitransparent film 42 having a certain transmittance are formed on a glass substrate 40. When the phase shift mask having patterns with different transmittances is to be inspected by an inspection apparatus using the above data comparison method, this phase shift mask cannot be inspected unless the defect detection sensitivity is lowered, as described above. This is because, when a positive type resist is used, both graphic data corresponding to the semitransparent film and the light-shielding film are set at level "0", and pattern data of the semitransparent film and the light-shielding film which are formed on the basis of the graphic data become equal to each other.

On the other hand, as shown in the light intensity distribution of FIG. 4B, a light intensity 43 of the region corresponding to the semitransparent film is higher than a light intensity 44 of the region corresponding to the light-shielding film. Therefore, when a conventional threshold value is applied to the absolute value of the difference between the intensity of a signal output from the line sensor and the pattern data, the phase shift mask is determined as a defective one because the absolute value of the difference of the region corresponding to the semitransparent film exceeds the threshold value. Therefore, when the defect detection sensitivity is lowered by decreasing the threshold value, a pseudo defect occurring when the semitransparent film is determined as a defective film can be prevented. However, the defect detection sensitivity for the light-shielding film is lowered, the defect detection sensitivities of the semitransparent film and the light-shielding film become different from each other.

SUMMARY OF THE INVENTION

It is an object of the present invention to provide an inspection apparatus which can detect a defect of a halftone type phase shift mask at high sensitivity and in which a semitransparent film and a light-shielding film have equal defect detection sensitivities, and a method therefor.

To achieve the object of the present invention, pattern inspection apparatus comprises:

a phase shift mask including patterns constituted by a light-shielding film and a semitransparent film;

means for radiating a beam on the phase shift mask;

converting means for converting a beam passing through the phase shift mask into an electrical signal;

a generation circuit for generating pattern data using synthesized graphic data output from the synthesizing means, the pattern data corresponding to a signal output from the converting means;

determining means for determining a pattern width on the basis of the graphic data;

correcting means in which a transmittance of the semitransparent film is set, the correcting means correcting the pattern data output from the generating means on the basis of the transmittance when the pattern width determined by the determining means is not more than a predetermined value; and comparing means for comparing corrected pattern data output from the correcting means with an output signal from the converting means, the comparing means detecting a defect of the patterns formed on the phase shift mask on the basis of a difference between the corrected pattern data and the output signal from the converting means.

According to the present invention, pattern data corresponding to the semitransparent film is corrected according to the transmittance of the semitransparent film. For this reason, a defect of the halftone type phase shift can be detected at high sensitivity, and the defect detection sensitivities of the semitransparent film and the light-shielding film can be equal to each other.

BRIEF DESCRIPTION OF THE DRAWINGS

The accompanying drawings, which are incorporated in and constitute a part of the specification, illustrate presently preferred embodiments of the invention, and together with the general description given above and the detailed description of the preferred embodiments given below, serve to explain the principles of the invention.

DETAILED DESCRIPTION OF THE PREFERRED EMBODIMENTS

Embodiments of the present invention will be described below with reference to the accompanying drawings.

Figure 1:
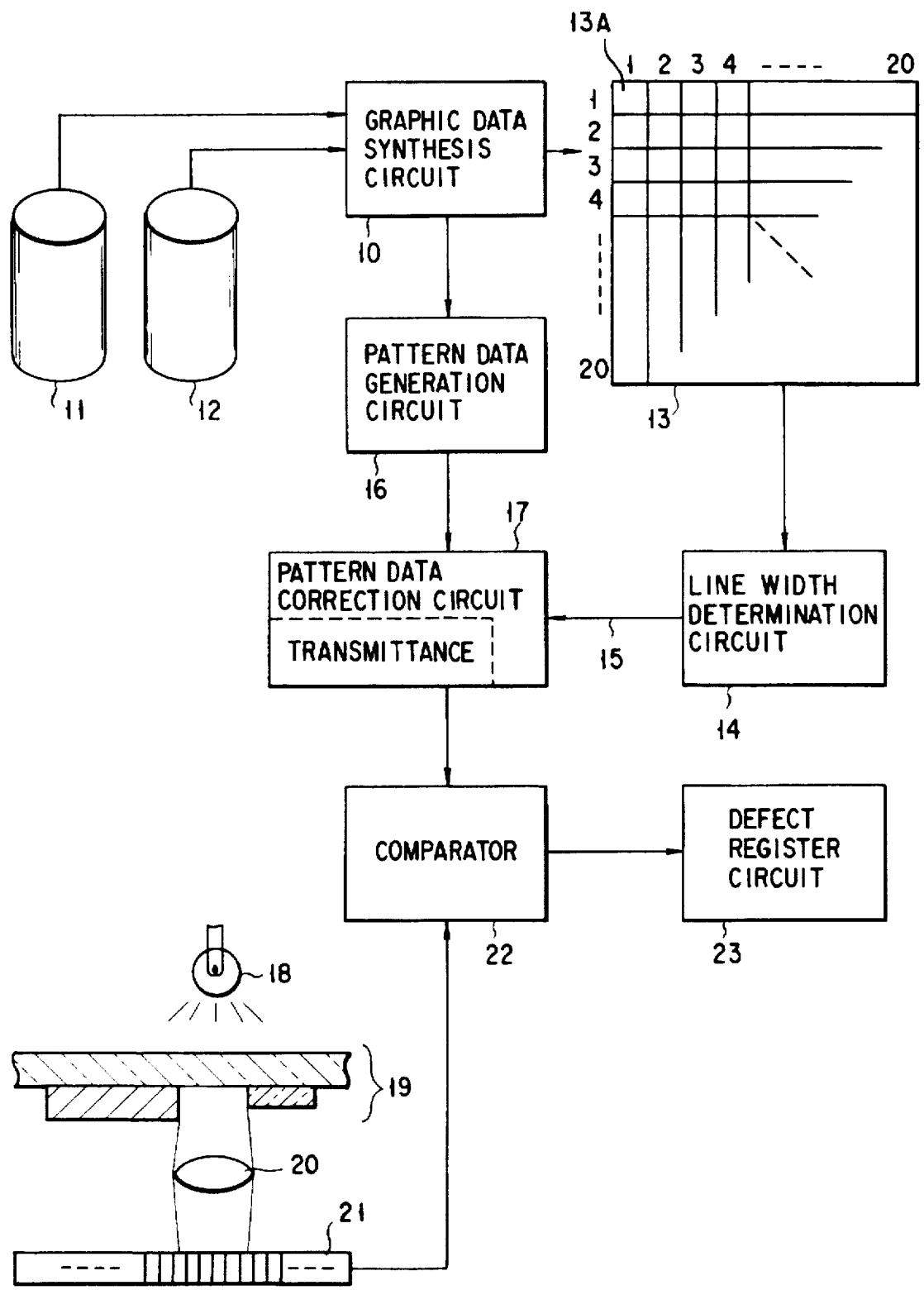
FIG. 1 is a view showing the arrangement of a pattern inspection apparatus according to the first embodiment of the present invention.

FIG. 1 is a view showing the arrangement of a pattern inspection apparatus according to an embodiment of the present invention. Referring to FIG. 1, graphic data for forming a light-shielding film is stored in a first memory 11, and graphic data for forming a semitransparent film is stored in a second memory 12. Each of these graphic data is constituted by coordinate data of a pattern to be formed and data representing a shape such as a rectangle, trapezoid, or triangle of the pattern. The first and second memories 11 and 12 are connected to a graphic data synthesis circuit (hereinafter referred to as a synthesis circuit) 10 for synthesizing the graphic data. The synthesis circuit 10 sequentially loads graphic data corresponding to inspection positions from the graphic data for the light-shielding film supplied from the first memory 11 and the graphic data for the semitransparent film supplied from the second memory 12, and converts these graphic data into bit patterns to synthesize them. That is, the synthesis circuit 10 synthesizes the bit pattern corresponding to the graphic data for the light-shielding film and the bit pattern corresponding to the graphic data for the semitransparent film using an AND logic.

Figure 2A:
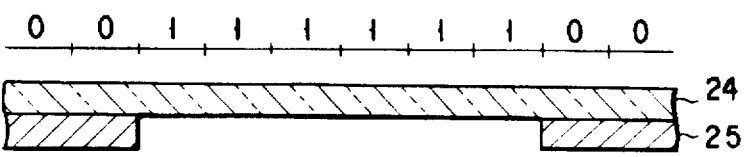
FIGS. 2A to 2C are views for explaining a method of synthesizing graphic data of a semitransparent film and a complete light-shielding film to generate graphic data of a halftone type phase shift mask.
Figure 2B:
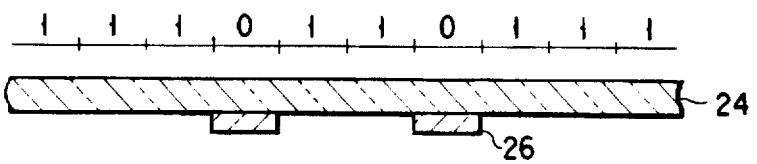
Figure 2C:
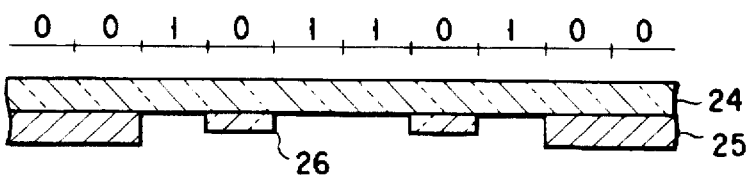
Figure 3A:
FIG. 3A is a sectional view showing a pattern of a photomask.
Figure 3B:
FIG. 3B is a view showing graphic data for forming the pattern shown in FIG. 3A.
Figure 3C:
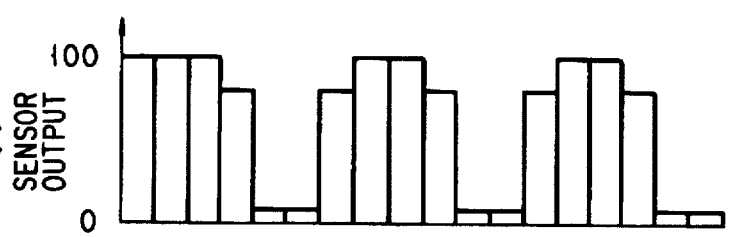
FIG. 3C is a graph showing an output from a line sensor corresponding to the pattern shown in FIG. 3A.
Figure 3D:
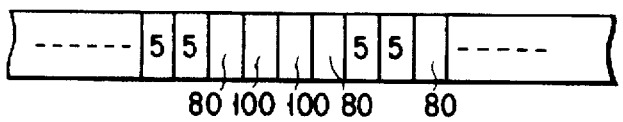
FIG. 3D is a chart showing pattern data corresponding to FIG. 3C.
Figure 4A:
FIG. 4A is a sectional view showing a halftone type phase shift mask.
Figure 4B:
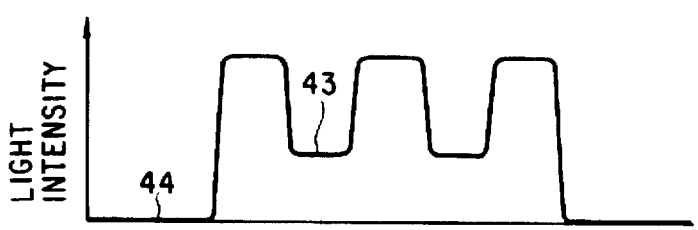
FIG. 4B is a graph showing a light intensity distribution obtained when an inspection beam is radiated on the halftone type phase shift mask shown in FIG. 4A.

In this case, the synthesis of the graphic data will be described below using the sectional views of photomasks shown in FIGS. 2A to 2C. In FIGS. 2A to 2C, patterns 25 and 26 are formed on a glass substrate 24. The pattern 25 is formed by a light-shielding film, and the pattern 26 is formed by a semitransparent film. Levels "0" and "1" indicate graphic data converted into bit patterns used for forming the patterns 25 and 26, respectively.

When the photomask having the shape shown in FIG. 2A is to be formed, a light-shielding film for forming the pattern 25 is formed on the entire surface of the glass substrate 24, and a positive type resist (not shown) is coated on the light-shielding film. Thereafter, an electron beam or a laser beam is radiated on the resist according to the graphic data, and the resist is developed. At this time, the resist in a region corresponding to level "1" of the graphic data is removed. Thereafter, when the light-shielding film is etched using the left resist as a mask, as shown in FIG. 2A, the pattern 25 constituted by the light-shielding film is formed in a region corresponding to level "0" of the graphic data.

The photomask shown in FIG. 2B is formed by using a semitransparent film in place of the light-shielding film shown in FIG. 2A, and the photomask shown in FIG. 2B is formed by the same method as that in FIG. 2A. Therefore, in the photomask shown in FIG. 2B, the pattern 26 constituted by the semitransparent film is formed in a region corresponding to level "0" of the graphic data.

The photomask shown in FIG. 2C is formed as follows. That is, after the photomask shown in FIG. 2A is formed on the surface of the glass substrate 24, the pattern 26 constituted by the semitransparent film is formed using the graphic data shown in FIG. 2B. This photomask is a halftone type phase shift mask having patterns constituted by the light-insulating film and the semitransparent film. The graphic data of this halftone type phase shift mask are obtained such that both the graphic data for forming the patterns 25 and 26 corresponding to the same region of the glass substrate 24 are synthesized using an AND logic. Either one of the patterns 25 and 26 is formed in a region corresponding to level "0" of the synthesized graphic data.

Referring back to FIG. 1, the arrangement of the pattern inspection apparatus will be described below. A third memory 13 is connected to the synthesis circuit 10. In the third memory 13, memory cells 13A are arranged in a matrix. Graphic data converted into bit patterns of the phase shift mask synthesized in the synthesis circuit 10 are sequentially stored in the third memory 13. A line width determination circuit 14 is connected to the third memory 13. This line width determination circuit 14 recognizes a pattern width, i.e., a line width, from the bit pattern stored in the third memory 13. If the recognized line width is a predetermined value or less, the determination circuit 14 determines a pattern having the line width as a halftone region. For example, when one unit of graphic data corresponds to 0.25×0.25 μm on a photomask, if the size of the third memory 13 is 20×20 dots, a pattern having a width of 5.0 μm can be determined. For a halftone type phase shift mask having a semitransparent film formed by a pattern with a line width of 2.5 μm or less, the line width determination circuit 14 determines a halftone region if a region in which data at level "0" are continuously written has 10 dots or less. When the line width determination circuit 14 determines a halftone region, it outputs a correction request signal 15 to a pattern data correction circuit 17.

Graphic data output from the synthesis circuit 10 is input to a pattern data generation circuit 16. This pattern data generation circuit 16 generates pattern data corresponding to an output signal from a line sensor 21 (to be described later) on the basis of the output signal from the synthesis circuit 10. That is, the pattern data generation circuit 16 recognizes, as a light-shielding region, a region corresponding to level "0" of the bit pattern supplied from the synthesis circuit 10 and recognizes, as a light-transmitting region, a region corresponding to level "1", thereby generating pattern data corresponding to the cells of the line sensor 21. The transmittance of the semitransparent film is stored in the pattern data correction circuit 17. When the pattern data correction circuit 17 receives the request signal 15 from the line width determination circuit 14, the signal level of pattern data, of pattern data supplied from the pattern data generation circuit 16, corresponding to the halftone region designated by the request signal 15 is corrected to a signal level corresponding to the semitransparent film in accordance with the transmittance of the semitransparent film. When the pattern data correction circuit 17 does not receive the request signal 15 from the line width determination circuit 14, the pattern data correction circuit 17 outputs the pattern data supplied from the pattern data generation circuit 16 without any change.

On the other hand, a Xe (xenon) lamp 18 radiates an inspection beam on a halftone type shift mask 19 to be inspected manufactured on the basis of the graphic data stored in the first and second memories. This inspection beam passes through the phase shift mask 19, and is received by the line sensor 21 through an objective lens 20. The line sensor 21 is constituted by a plurality of photoelectric conversion elements, and each element outputs a signal at a level corresponding to the intensity of the transmitted beam received by the corresponding element. An output signal from the line sensor 21 is supplied to a comparator 22 together with the pattern data output from the pattern data correction circuit 17. The comparator 22 calculates the difference between the level of the output signal from the line sensor 21 and the signal level of the pattern data. When the absolute value of this difference exceeds a predetermined threshold value, position data on that portion of the phase shift mask 19, which relates to this absolute value of this difference exceeding the predetermined threshold value, is registered in a defect register circuit 23.

According to the above embodiment, the pattern data correction circuit 17 corrects the pattern data corresponding to the semitransparent film and generated by the pattern data generation circuit 16 in response to an output signal from the line width determination circuit 14 in accordance with the transmittance of the semitransparent film. Therefore, since pattern data corresponding to the patterns constituted by the light-shielding film and the semitransparent film are caused to be different from each other in accordance with the transmittance, detection of a pseudo defect can be prevented without increasing the threshold value unlike in the conventional method.

According to this embodiment, since the threshold value need not be increased even when a photomask includes a semitransparent film, a defect can be detected at high sensitivity. In addition, since the pattern data corresponding to the pattern constituted by the semitransparent film is corrected, the defect detection sensitivities of the patterns of the semitransparent film and the light-shielding film can be caused to be equal to each other.

Figure 5:
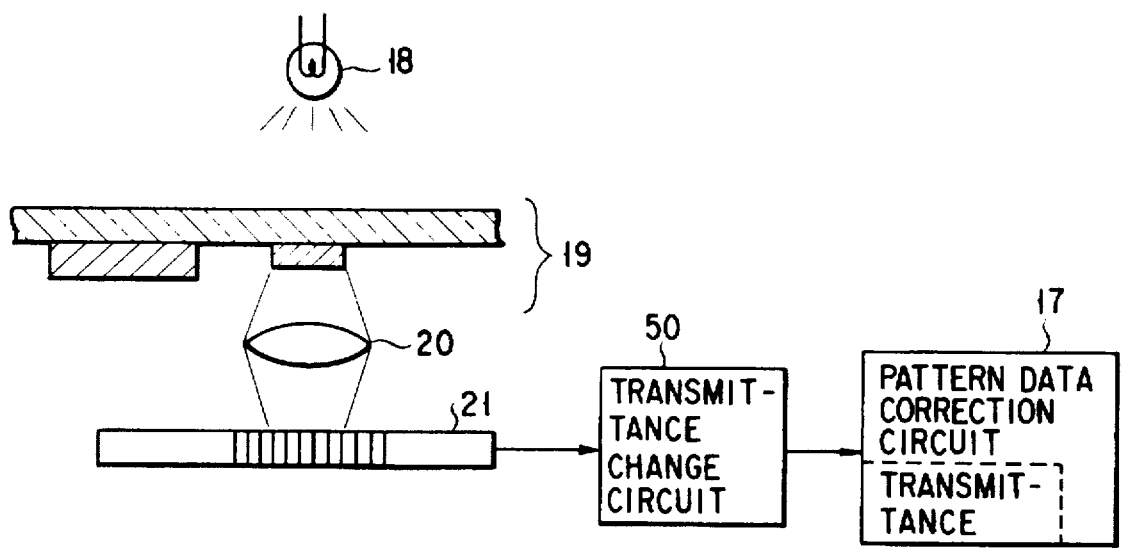
FIG. 5 is a view showing the arrangement of a main part of the second embodiment of the present invention.

FIG. 5 shows the second embodiment of the present invention. Although the above pattern inspection apparatus uses the Xe lamp 18 as a light source, the pattern inspection apparatus inspects halftone type phase shift masks used in various exposure apparatuses. For this reason, the inspection apparatus and the exposure apparatus may use different light sources. In this case, an exposure beam and an inspection beam have different wavelengths. In addition, a semitransparent film has a transmittance which changes depending on the wavelength of a beam. For this reason, when the transmittance of a semitransparent film prestored in the pattern data correction circuit 17 corresponds to that of the exposure beam from the exposure apparatus, appropriate correction is not performed.

According to the second embodiment, as shown in FIG. 5, a transmittance change circuit 50 is connected between a line sensor 21 and a pattern data correction circuit 17. Prior to pattern inspection, a Xe lamp 18 radiates an inspection beam on a halftone type phase shift mask 19. The transmittance change circuit 50 detects the intensity of a signal corresponding to a pattern constituted by the semitransparent film in accordance with an output from the line sensor 21, and changes transmittance stored in the pattern data correction circuit 17 on the basis of the detected intensity of the signal. With the above arrangement, even when the wavelengths of an exposure beam and an inspection beam are different from each other, inspection can be reliably performed.

The third embodiment of the present invention will be described below. The graphic data of a light-shielding film and a semitransparent film for forming one halftone type phase shift mask are not always formed by one file. Normally, a region on a mask is divided into a plurality of regions, and files constituted by the graphic data for forming the patterns of the light-shielding film and the semitransparent film are formed in units of divided regions. Some divided regions have patterns constituted by only a semitransparent film, and some others have patterns constituted by only a light-shielding film.

Figure 6:
FIG. 6 is a view showing the arrangement of the third embodiment of the present invention and showing a correction identifier.

FIG. 6 shows a file constituted by graphic data of a halftone region having a pattern constituted by only a semitransparent film. A correction identifier ID indicating the graphic data of the halftone region is added to this file.

Figure 7:
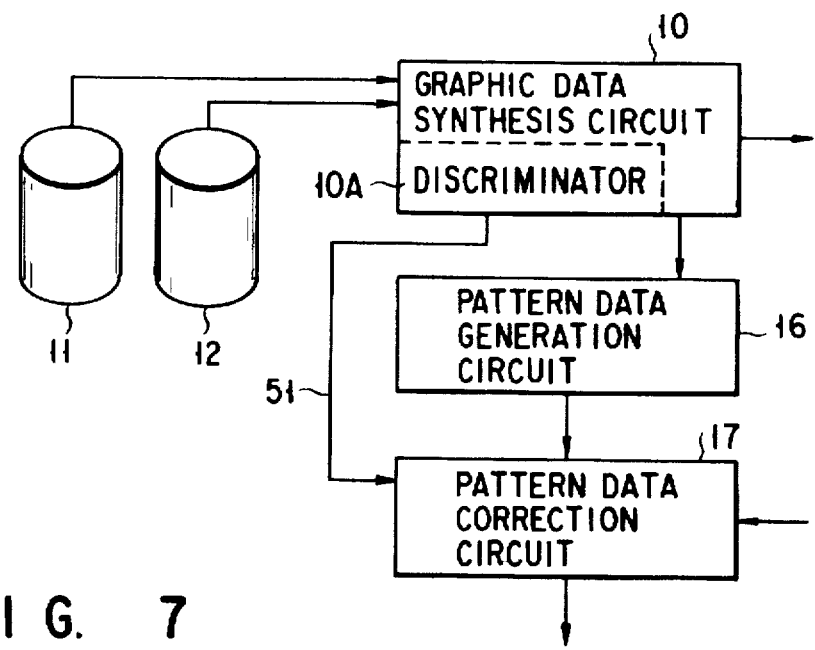
FIG. 7 is a view showing the arrangement of a main part of the third embodiment of the present invention.

On the other hand, for example, a discriminator 10A is arranged in a synthesis circuit 10, as shown in FIG. 7. This discriminator 10A checks whether a correction identifier ID is added to the file read from a second memory 12 into the synthesis circuit 10. When it is determined as the discrimination result that a correction identifier ID is present, the synthesis circuit 10 does not output graphic data converted into a bit pattern to a memory 13. In addition, a pattern data generation circuit 16 generates pattern data from the graphic data supplied from the synthesis circuit 10, and a pattern data correction circuit 17 corrects all pattern data supplied from the pattern data generation circuit 16 in response to an output signal 51 from the discriminator 10A.

According to this embodiment, the graphic data of a halftone region having a pattern constituted by only a semitransparent film is not stored in the memory 13, nor determined by a line width determination circuit 14, and the pattern data correction circuit 17 corrects all pattern data supplied from the pattern data generation circuit 16. Therefore, a period of time required for correcting the pattern data can be shortened.

What is claimed is:

1. A pattern inspection apparatus comprising:

a phase shift mask including a transparent substrate and patterns formed on said transparent substrate, said patterns being constituted by a light-shielding film and a semitransparent film;

means for radiating a beam on said phase shift mask;

converting means for converting a beam passed through said phase shift mask into an electrical signal, and for outputting first pattern data corresponding to said electrical signal;

storing means for storing graphic data for forming patterns constituted by said light-shielding film and said semitransparent film;

generating means for generating second pattern data using said graphic data supplied from the storing means, said second pattern data corresponding to locations of said phase shift mask where light is transmitted and not transmitted;

determining means for determining a pattern width of said second pattern data generated by said generating means on the basis of said graphic data supplied from said storing means, wherein said determining means determines said second pattern data having said pattern width as said semitransparent film when said pattern width is not more than a predetermined value, and for outputting a correction request signal;

correcting means in which a transmittance value of the semitransparent film is stored, said correcting means correcting said second pattern data output from said generating means on the basis of said transmittance value to account for light transmitted through said semitransparent film when said correction request signal is supplied from said determining means; and comparing means for comparing said corrected second pattern data output from said correcting means with said first pattern data output from said converting means, said comparing means detecting a defect in said patterns formed on said phase shift mask on the basis of differences between said corrected second pattern data output from said generating means and said first pattern data output from said converting means.

2. The apparatus according to claim 1, wherein said graphic data includes first and second graphic data, and wherein said storing means includes:

first storing means for storing said first graphic data for forming a pattern constituted by said light-shielding film; and second storing means for storing said second graphic data for forming a pattern constituted by said semitransparent film.

3. The apparatus according to claim 2, further comprising:

synthesizing means for synthesizing said first and second graphic data stored in said first and second storing means, said synthesizing means converting said synthesized first and second graphic data into bit patterns; and third storing means having a plurality of memory cells arranged in a matrix, said third storing means storing said bit patterns supplied from said synthesizing means, and wherein said determining means determines a pattern width on the basis of the number of continuous bits at the same level from said bit patterns stored in said third storing means.

4. The apparatus according to claim 2, wherein the second graphic data has an identifier indicating data constituted by only the semitransparent film.

5. An apparatus according to claim 4, further comprising:

discriminating means for discriminating whether said second graphic data has said identifier or not, when said second graphic data has said identifier, said discriminating means outputs a signal to said correcting means, so that said correcting means corrects all second pattern data generated by said generating means in accordance with the transmittance value of the semitransparent film.

6. The apparatus according to claim 1, further comprising:

changing means, connected to said correcting means and said converting means, for changing said transmittance value of said semitransparent film stored by said correcting means, said changing means changing said transmittance value of said semitransparent film on the basis of an intensity of a signal corresponding to light transmitted by said semitransparent film and the first pattern data output from said converting means.

7. A pattern inspection apparatus comprising:

a phase shift mask including a transparent substrate and patterns formed on said transparent substrate, said patterns including a light-shielding film and a semitransparent film, wherein a pattern width of said semitransparent film is equal to or narrower than that of said light-shielding film;

radiating means for radiating a beam on said phase shift mask;

converting means for converting a beam passed through said phase shift mask into an electrical signal, and for outputting a pattern data corresponding to said electrical signal;

first storing means for storing first graphic data for forming said light-shielding pattern constituted by said light-shielding film;

second storing means for storing second graphic data for forming semitransparent pattern constituted by said semitransparent film;

synthesizing means for synthesizing said first and second graphic data stored in said first and second storing means, said synthesizing means converting the synthesized first and second graphic data into bit patterns;

third storing means having a plurality of memory cells arranged in a matrix, said third storing means storing the bit patterns supplied from said synthesizing means;

determining means for determining a pattern width on the basis of the number of continuous bits at the same level from the bit patterns stored in said third storing means, and for outputting a correction request signal when the number is not more than a predetermined value;

generating means for generating pattern data using the synthesized first and second graphic data outputs from said synthesizing means;

correcting means in which a transmittance value of the semitransparent film is stored, said correcting means correcting pattern data output from said generating means on the basis of the transmittance value to account for the light transmitted through the semitransparent film when the correction request signal is supplied from the determining means; and comparing means for comparing the corrected pattern data output from said correcting means with the pattern data output from said converting means, said comparing means detecting a defect of the pattern formed on said phase shift mask on the basis of a difference between the corrected pattern data and the pattern data output from said converting means.

8. An apparatus according to claim 2, further comprising:

synthesizing means for synthesizing the first and second graphic data stored in said first and second storing means, said synthesizing means converting the synthesized first and second graphic data into bit patterns; and third storing means having a plurality of memory cells arranged in a matrix, said third storing means storing said bit patterns supplied from said synthesizing means.

9. The apparatus according to claim 1, wherein said first pattern data has first and second values, and wherein said first value corresponds to said light-shielding film, and said second value corresponds to said semitransparent film.

10. The apparatus according to claim 1, wherein said second pattern data includes third and fourth values, said third value corresponding to a first location of light that is transmitted and said fourth value corresponding to a second location of light that is not transmitted.

11. The apparatus according to claim 10, wherein said correction means corrects said fourth value of said second pattern data on the basis of said transmittance value.

12. The apparatus according to claim 1, wherein said comparing means for detecting a difference between said corrected second pattern data output from said correcting means and said first pattern data output from said converting means outputs position data to identify a defect portion of said phase shift mask when said difference exceeds a predetermined value.

13. A method of inspection of a phase shift mask for defects, comprising the steps of:

forming pattern data from graphic data, said graphic data used for drawing patterns of a phase shift mask including a transparent substrate and patterns formed on said transparent substrate, said patterns being constituted by a light-shielding film and a semitransparent film, said pattern data corresponding to portions of said phase shift mask where light is transmitted and where light is not transmitted by a beam passing through said phase shift mask;

detecting a portion of said pattern data where the patterns of the phase shift mask are constituted by said semitransparent film;

correcting said pattern data portion in accordance with a transmittance value to account for light transmitted through said semitransparent film when said portion is detected; and comparing an intensity of the transmitted beam from said phase shift mask with said corrected pattern data portion to determine whether defects exist in said patterns of said phase shift mask.

14. The method according to claim 13, wherein said correcting step also includes the step of determining, when a width of said patterns is not more than a predetermined value, and correcting said pattern data corresponding to said patterns in accordance with said transmittance value of said semitransparent film.

15. The method according to claim 13, wherein said correcting step also includes the steps of determining, when the pattern data is constituted by the semitransparent film, and correcting said pattern data in accordance with said transmittance value of the semitransparent film.

16. The method according to claim 13, further including the step of:

measuring an intensity of a beam passing through a pattern portion constituted by the semitransparent film to correct said transmittance value prior to the inspection.

17. An apparatus according to claim 1, wherein a pattern width of said semitransparent film is equal to or narrower than that of said light-shielding film.

18. A method according to claim 13, wherein a pattern width of said semitransparent film is equal to or narrower than that of said light-shielding film.

* * * * *